US00PP23492P2

(12) United States Plant Patent
Nishikawa

(10) Patent No.: US PP23,492 P2
(45) Date of Patent: Mar. 19, 2013

(54) ***DELOSPERMA* PLANT NAMED 'JEWEL OF DESERT TOPAZ'**

(50) Latin Name: *Delosperma cooperi*
Varietal Denomination: Jewel of Desert Topaz

(75) Inventor: Koichiro Nishikawa, Quito (EC)

(73) Assignee: Ronvandijk Consultancy B.V., Boskoop (NL)

( * ) Notice: Subject to any disclaimer, the term of this patent is extended or adjusted under 35 U.S.C. 154(b) by 0 days.

(21) Appl. No.: 13/199,826

(22) Filed: Sep. 9, 2011

(51) Int. Cl.
*A01H 5/00* (2006.01)

(52) U.S. Cl. ..... Plt./422

(58) Field of Classification Search ..... Plt./422
See application file for complete search history.

*Primary Examiner* — Howard Locker
(74) *Attorney, Agent, or Firm* — Penny J. Aguirre

(57) ABSTRACT

A new cultivar of *Delosperma* plant, 'Jewel of Desert Topaz', characterized by its compact and very horizontal plant habit, its relatively small leaves, its very floriferous and long blooming flowering habit, and its flowers that are yellow-orange in color with red petal tips, white-light purple centers, and yellow anthers.

2 Drawing Sheets

Botanical classification: *Delosperma cooperi.*
Variety denomination: 'Jewel of Desert Topaz'.

CROSS REFERENCE TO RELATED APPLICATIONS

This application is co-pending with U.S. Plant Patent Applications filed for plants derived from the same breeding program that are entitled *Delosperma* Plant Named 'Jewel of Desert Rosequartz' (U.S. Plant patent application Ser. No. 13/199,787), *Delosperma* Plant Named 'Jewel of Desert Moon Stone' (U.S. Plant patent application Ser. No. 13/199,823), *Delosperma* Plant Named 'Jewel of Desert Ruby' (U.S. Plant patent application Ser. No. 13/199,812), *Delosperma* Plant Named 'Jewel of Desert Peridot' (U.S. Plant patent application Ser. No. 13/199,815), and *Delosperma* Plant Named 'Jewel of Desert Garnet' (U.S. Plant patent application Ser. No. 13/199,846).

BACKGROUND OF THE INVENTION

The present invention relates to a new and distinct cultivar of *Delosperma* plant, botanically known as *Delosperma cooperi* 'Jewel of Desert Topaz' and will be referred to hereinafter by its cultivar name, 'Jewel of Desert Topaz'. The new cultivar of *Delosperma* is an herbaceous perennial grown for container and landscape use.

The new cultivar was derived from a controlled breeding program conducted by the Inventor in Ichinimiya-City, Aichi-Pref, Japan. The overall purpose of the breeding program was to develop new cultivars of *Delosperma* plants with low-growing and well-spreading growth habits combined with long flowering periods and a unique range of flower colors.

'Jewel of Desert Topaz' was selected in the Inventor's trial garden in November 2006 as a single unique plant from amongst the seedlings derived from self-crossing an unnamed plant from the Inventor's breeding program in May 2005. The Inventor's reference code for the parent plant is "A".

Asexual propagation of the new cultivar was first accomplished by softwood cuttings in 2009 by the Inventor in Ichinimiya-City, Aichi-Pref, Japan. Propagation by softwood cuttings has shown that the unique features of the new cultivar are stable and reproduced true to type in successive generations.

SUMMARY OF THE INVENTION

The following traits have been repeatedly observed and are determined to be the characteristics of the new cultivar. These attributes in combination distinguish 'Jewel of Desert Topaz' as a unique cultivar of *Delosperma.*

1. 'Jewel of Desert Topaz' exhibits a compact and very horizontal plant habit.
2. 'Jewel of Desert Topaz' exhibits relatively small leaves.
3. 'Jewel of Desert Topaz' exhibits a very floriferous and long blooming flowering habit.
4. 'Jewel of Desert Topaz' exhibits flowers that are yellow-orange in color with red petal tips, white-light purple centers, and yellow anthers.

The parent plant of 'Jewel of Desert Topaz', Ref. code "A", differs from 'Jewel of Desert Topaz' in having a more upright (less horizontal) plant habit, in blooming for a shorter time period, and in having flowers that are light yellow in color with white centers. 'Jewel of Desert Topaz' can be most closely compared to the cultivar 'Reiko' (not patented), which is similar to 'Jewel of Desert Topaz' in having a horizontal plant habit. 'Reiko' differs from 'Jewel of Desert Topaz' in having a less regular plant habit, purple flowers and in blooming for a shorter period of time.

'Jewel of Desert Topaz' can also be compared to cultivars with co-pending patent applications from the same breeding program that differ from 'Jewel of Desert Topaz' most significantly in flower color:

'Jewel of Desert Ruby' has red flowers with deep pink and white centers and yellow anthers.

'Jewel of Desert Moon Stone' has white flowers with yellow anthers.

'Jewel of Desert Rosequartz' has light pink flowers with white centers and yellow anthers.

'Jewel of Desert Peridot' has yellow flowers with white centers and yellow anthers.

'Jewel of Desert Garnet' has red-orange flowers with pink centers and yellow anthers.

BRIEF DESCRIPTION OF THE DRAWINGS

The accompanying colored photographs illustrate the overall appearance and distinct characteristics of the new *Delosperma*. The plant in the photograph is 3 months in age as grown in a 7-cm container in a unheated greenhouse in Noordwijkerhout, The Netherlands.

The photograph in FIG. 1 provides a side view of 'Jewel of Desert Topaz' in bloom.

Figure 1:
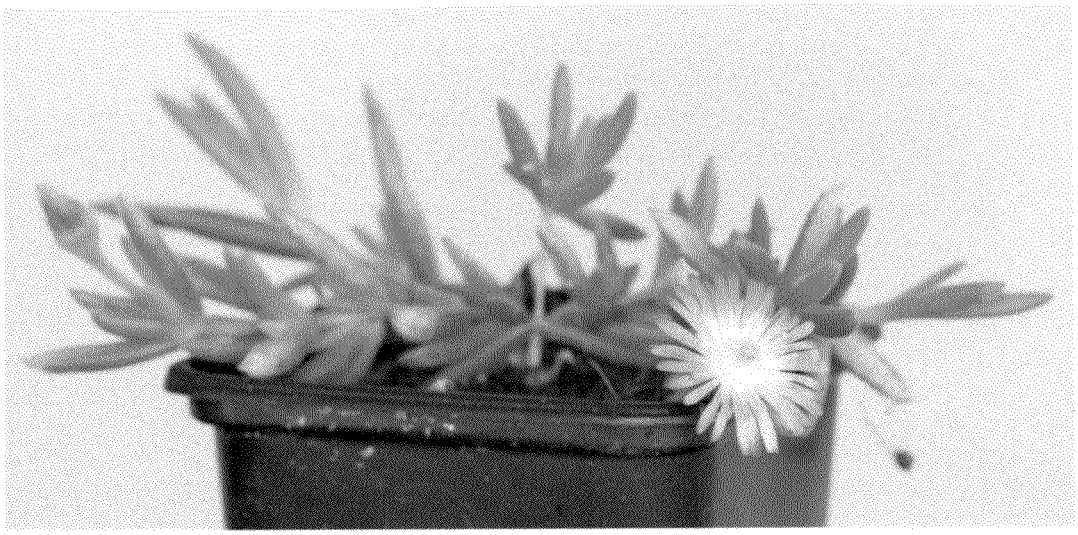
Figure 2:
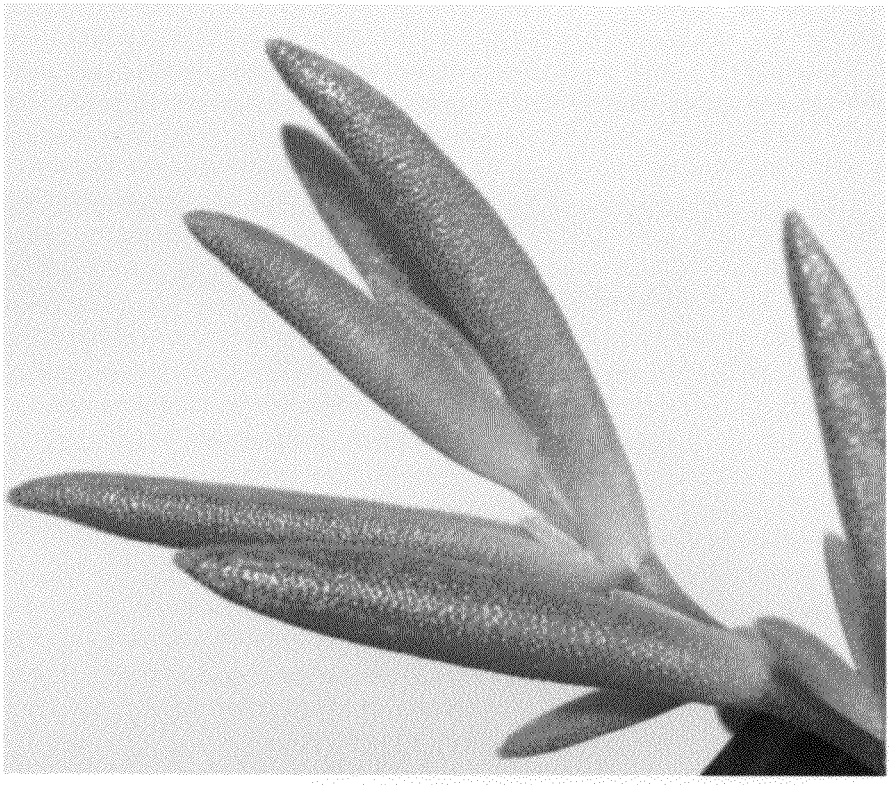

The photograph in FIG. 2 provides a close-up view of the foliage of 'Jewel of Desert Topaz'.

Figure 3:
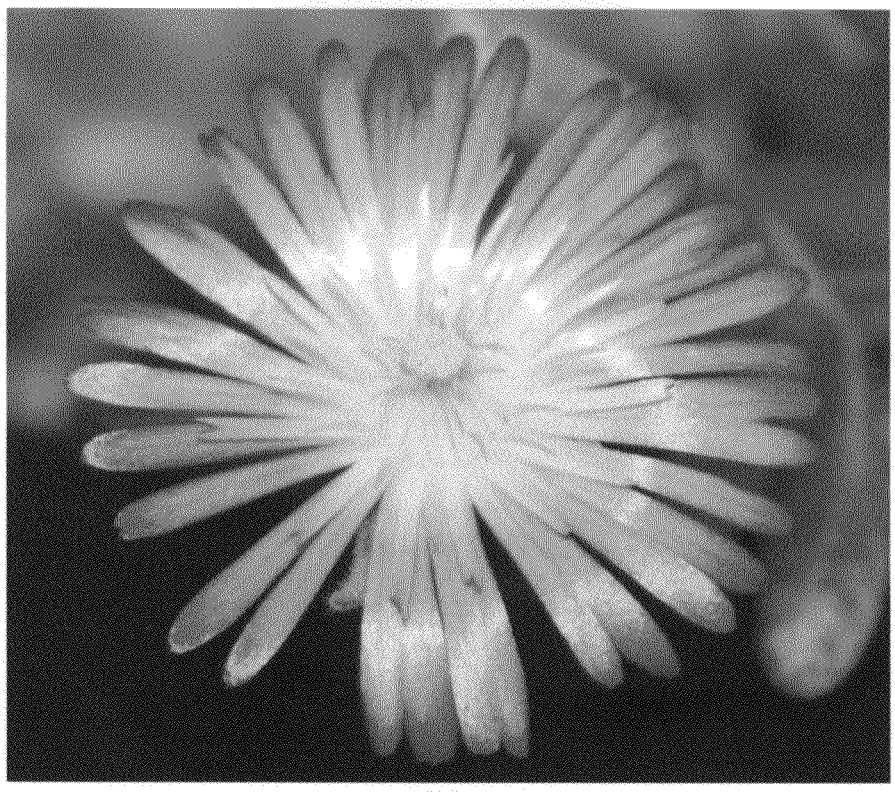

The photograph in FIG. 3 provides a close-up view of a flower of 'Jewel of Desert Topaz'.

The colors in the photographs may differ slightly from the color values cited in the detailed botanical description, which accurately describe the colors of the new *Delosperma.*

DETAILED BOTANICAL DESCRIPTION

The following is a detailed description of three month-old plants of the new cultivar as grown in 7-cm containers in a unheated greenhouse in Noordwijkerhout, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Mid April to mid September in Noordwijkerhout, The Netherlands.

*Plant type*.—Herbaceous perennial.

*Plant habit*.—Compact, well-spreading, horizontal.

*Height and spread*.—Reaches about 5 cm in height and about 10.3 cm in diameter with mature plants reaching up to 10 cm in height and 30 cm in spread.

*Cold hardiness*.—Observed to be hardy to U.S.D.A. Zone 7.

*Diseases*.—No more susceptible or resistant to diseases than other *Delosperma cooperi* varieties, diseases are typically not a problem for *Delosperma cooperi*, except when grown with too much moisture.

*Root description*.—Fibrous roots.

*Propagation*.—Softwood cuttings.

*Growth habit*.—Moderately vigorous.

Stem description:

*Shape*.—Round.

*Stem color*.—A blend of 147C and 147D, older stems 177D.

*Stem size*.—Lateral branches; an average of 3.8 cm in length and 2 mm in diameter.

*Stem surface*.—Moderately glossy, moderately covered with very short glandular hairs; average of 0.2 mm in length, 155C in color.

*Branching habit*.—Freely branching, average of 4 lateral branches, 3.8 cm in length and 2 mm in diameter, branch internode length is variable but typically about 1.0 cm.

Foliage description:

*Leaf shape*.—Ligulate, triangular in diameter, succulent.

*Leaf division*.—Simple.

*Leaf base*.—Cuneate.

*Leaf apex*.—Acute.

*Leaf venation*.—No veins visible.

*Leaf margins*.—Entire.

*Leaf arrangement*.—Opposite.

*Leaf surface* (*upper and lower surface*).—Slightly glossy, slightly pubescent with very short glandular hairs, average length about 0.2 mm, 155C in color.

*Leaf color*.—Young upper and lower surface; a blend of 143B and 143C, base 144B, mature upper and lower surface; a blend of 143A and 143B.

*Leaf size*.—About 2.8 cm in length and 4.5 mm in width.

*Leaf quantity*.—Average of 8 per lateral branch (4 pairs).

*Leaf attachment*.—Sessile.

Inflorescence description:

*Inflorescence type*.—Flowers solitary, rotate.

*Flower number*.—Average of 3 per lateral stem and 12 per plant.

*Flower fragrance*.—Moderately faint, sweet and pleasant.

*Flower aspect*.—Outward to upright.

*Flower longevity*.—A few days.

*Flower type*.—Single.

*Flower size*.—Average of 2.7 cm in diameter and 1.0 cm in depth.

*Flower buds*.—Broad ovate to oblong in shape, average of 2 per lateral system, average of 11 mm in length and 6 mm in diameter, color; 145A, flushing upward becoming a blend of 143A to 143B.

*Sepals*.—5, ovate in shape, margin entire, average of 5 mm in length and 2.5 mm in width, broadly acute apex, broadly cuneate base, surface is smooth and dull on upper and lower surface, color; young upper and lower surface; a blend of 145A and 143A to 143B near apex, mature upper surface; 146B, mature lower surface; a blend of 145A to 146C and 143A near apex.

*Petals*.—An average of 30 per flower, rotate and slightly curved arrangement, narrow oblanceolate in shape, surface smooth on upper and lower, margin entire, apex is obtuse, average of 1.3 cm in length and 2 mm in width, color opening and fully opened upper surface; a blend of 26A and 14A, base 75B to 75C blending with 155A, apex flushed with 178B, opening flowers and fully opened lower surface; 63B with base of petal 63C to 63D, fading upper surface; a blend of 26C and 14A, base 75C blending with 155A, fading lower surface; 63C with base 63D.

*Petaloid*.—Rotate near vertical and placed around stamens, average of 30, lanceolate in shape, margin entire, apex obtuse, base truncate, upper and lower surface smooth, average of 4 mm in length and 1 mm in width, color upper and lower mature and immature surface; 62D blended with 155A, non fading.

*Calyx*.—Rotate in shape, average of 6 mm in length and 1.5 cm in diameter.

*Peduncle*.—Average of 3.2 cm in length and 1.5 mm in diameter, straight on top of lateral branch at 0°, 144C in color, surface moderately glossy, moderately covered with very short glandular hairs.

Reproductive organs:

*Pistils*.—About 5, average of 2 mm in length, triangular shaped stigma, style is an average of 2 mm in length and 144A in color, and ovary is 143C in color.

*Stamens*.—Average of 60, anthers are dorsifixed and narrow oblong in shape, average of 0.5 mm in diameter, and 13A in color, filaments are 2 mm in length and 155D in color, pollen is moderate in quantity and 14A to 14B in color.

*Fruit*.—Fruit and seed production was not observed under the conditions tested.

It is claimed:

1. A new and distinct variety of *Delosperma* plant named 'Jewel of Desert Topaz' as described and illustrated herein.

* * * * *